United States Patent [19]

Hibino et al.

[11] Patent Number: 5,241,075
[45] Date of Patent: Aug. 31, 1993

[54] PHOTOCHROMIC SPIROPYRAN COMPOUNDS

[75] Inventors: Junichi Hibino; Eiji Ando, both of Osaka, Japan

[73] Assignee: Matsushita Electric Industrial Co., Ltd., Osaka, Japan

[21] Appl. No.: 869,079

[22] Filed: Apr. 14, 1992

Related U.S. Application Data

[63] Continuation of Ser. No. 558,362, Jul. 27, 1990, abandoned.

[30] Foreign Application Priority Data

Jul. 31, 1989 [JP] Japan ................... 1-198984

[51] Int. Cl.$^5$ .......................... C07D 491/107
[52] U.S. Cl. ................................... 548/409
[58] Field of Search ......................... 548/409

[56] References Cited

U.S. PATENT DOCUMENTS 3,933,509  1/1976  Noguchi et al. ............. 548/409

FOREIGN PATENT DOCUMENTS 1374437  11/1974  United Kingdom .

OTHER PUBLICATIONS

Patent Abstracts of Japan vol. 13, No. 15 (C-559)(3363) Jan. 13, 1989, & JP-A-63 221192 (Sony Corp.) Sep. 14, 1988.

*Primary Examiner*—Mukund J. Shah
*Assistant Examiner*—Matthew V. Grumbling
*Attorney, Agent, or Firm*—Lowe, Price, LeBlanc & Becker

[57] ABSTRACT

Novel photochromic spiropyran compounds having an absorption sensitivity in a longer wavelength region than known photochromic compounds are provided. The novel spiropyran compounds have a spiropyran skeleton having a methoxy group at the 6 position, a nitro group at the 8 position, a bromine atom at the 5' and 7' positions, and an alkyl group at the 1' position.

2 Claims, 1 Drawing Sheet

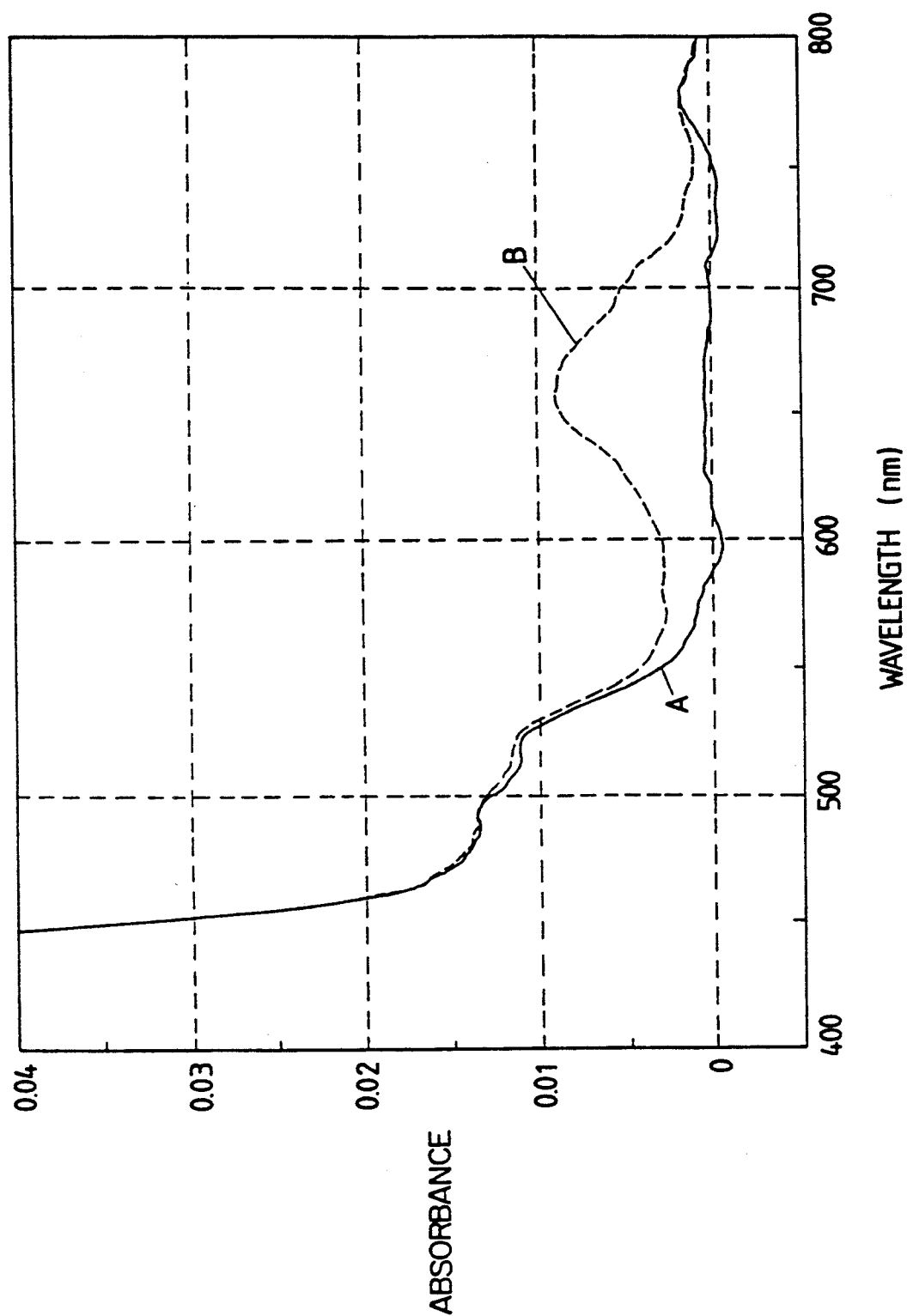

PHOTOCHROMIC SPIROPYRAN COMPOUNDS

This application is a continuation of application Ser. No. 07/558,362 filed Jul. 27, 1990 abandoned.

BACKGROUND OF THE INVENTION

1. Field of the Invention

This invention relates to photochromic materials and more particularly, to novel photochromic spiropyran compounds.

2. Description of the Prior Art

Photochromic materials are known as those materials which undergo reversible changes in color. One of typical photochromic materials includes spiropyran compounds. A number of spiropyran compounds have been studied and developed up to now. For instance, when a spiropyran compound of the following formula (A) is irradiated with UV light with a wavelength of 340 nm, it is changed into the merocyanine of the formula (B) assuming a red color. When visible light with a wavelength of 580 nm is again applied to the merocyanine, it is returned to the spiropyran (A).

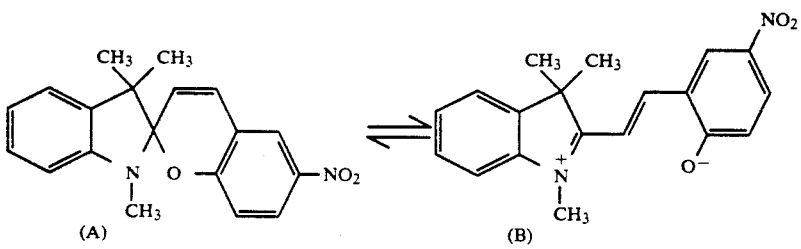

This property of the photochromic materials can be utilized to fabricate optical storage media. In order to miniaturize the medium, it is desirable to use a semiconductor laser as a light source for the storage media. To this end, it is necessary that photochromic materials have an absorption sensitivity in the vicinity of 700 nm which is in an oscillation region of the semiconductor laser.

SUMMARY OF THE INVENTION

It is accordingly an object of the invention to provide novel photochromic spiropyran compounds which exhibit good absorption sensitivity to light in a longer wavelength range than known photochromic spiropyran compounds.

It is another object of the invention to provide novel spiropyran compounds which have a methoxy group at the 6 position of the spiropyran skeleton, a nitro group at the 8 position, a bromine atom at the 5' and 7' positions and an alkyl group at the 1' position.

According to the invention, there is provided a novel photochromic spiropyran compound of the following formula (I)

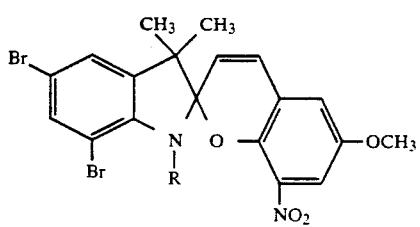

wherein R represents an alkyl group having from 1 to 30 carbon atoms.

BRIEF DESCRIPTION OF THE DRAWING

The sole FIGURE is a UV to visible light absorption spectrum chart of a novel spiropyran compound (SP-B) according to the invention in a colorless state (A) and in a colored state (B) in dimethylformamide.

DETAILED DESCRIPTION AND EMBODIMENTS OF THE INVENTION

Once again, the novel spiropyran compound of the invention has the following general formula

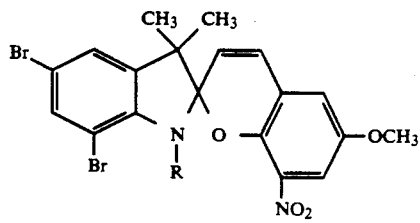

wherein R represents an alkyl group having from 1 to 30 carbon atoms. In view of the sensitivity and the preparation in high yield, the alkyl group represented by R has preferably from 16 to 20 carbon atoms.

The preparation of a spiropyran having the following structural formula (hereinafter abbreviated as SP-B) according to a process including the following five steps is described step by step.

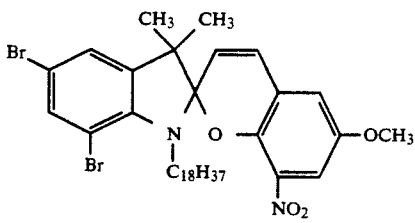

STEP 1

42.3 g (266 mmols) of 2,3,3-trimethyl indolenine of the formula (1) and 101.1 g (266 mmols) of iodooctadecane of the formula (2) are dissolved in 200 ml of 2-butanone, followed by heating under reflux for 40 hours. After removal of the 2-butanone by distillation, the resultant solid residue is recrystallized from 1000 ml of ethanol to obtain 91.5 g (197 mmols, yield 63.9%) of a reddish white solid of 1-octadecyl-2,3,3-trimethylindolenium iodide of the formula (3). The above reaction is shown below.

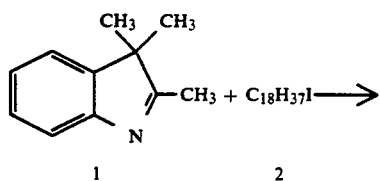

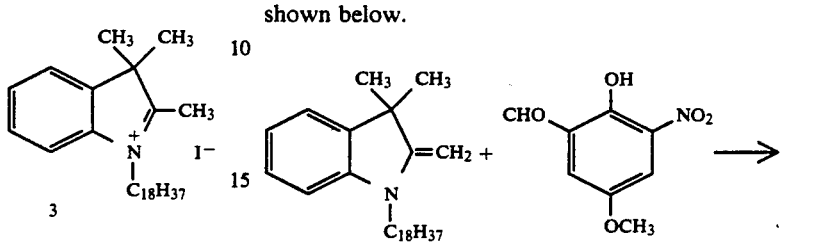

STEP 2

91.5 g (197 mmols) of 1-octadecyl-2,3,3-trimethylindolenium iodide of the formula (3) is dispersed in 100 ml of diethyl ether, followed by further dispersion in 400 ml of a 3.8N sodium hydroxide aqueous solution. After agitation for 3.5 hours, the resultant oil layer or phase is extracted with diethyl ether, followed by drying over day and night with use of sodium hydroxide. Thereafter, the diethyl ether is distilled off to obtain 65.6 g (159 mmols, yield 80.7%) of a yellow liquid of 1-octadecyl-2-methylene-3,3-dimethylindoline of the formula (4) as shown below.

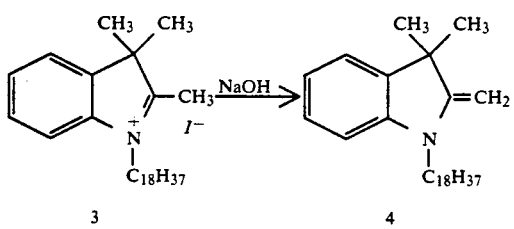

STEP 3

8.0 g (52.6 mmols) of 5-methoxysalicylaldehyde of the formula (5) are dissolved in 50 ml of acetic acid and violently agitated while keeping the reaction solution at about 15° C. with use of iced water, followed by dropping a solution of 2.5 ml (59.7 mmols) of fuming sulfuric acid (d=1.52, 99%) in 8 ml of acetic acid in one hour. Thereafter, the agitation was continued for further 7 hours. The resultant precipitate was filtered, followed by recrystallization from 500 ml of ethanol to obtain 4.2 g (21.3 mmols, yield 40.5%) of yellow needle crystals of 3-nitro-5-methoxysalicylaldehyde (6) as shown below.

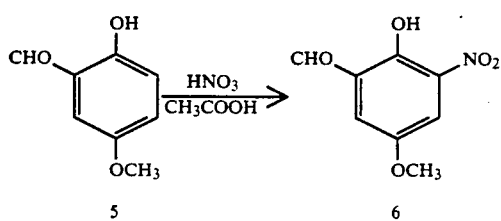

STEP 4

2 g (4.9 mmols) of the 1-octadecyl-2-methylene-3,3-dimethylindoline of the formula (4) obtained through Steps 1 and 2 and 0.8 g (4.1 mmols) of 3-nitro-5-methoxysalicylaldehyde obtained in Step 3 are heated under reflux in 20 ml of ethanol. The resultant dark green reaction solution is cooled and the resulting precipitate is recrystallized from 80 ml of ethanol three times to obtain 1.6 g (2.7 mmols, yield 65.9%) of spiropyran 7 as yellowish brown crystals. The reaction sequence is shown below.

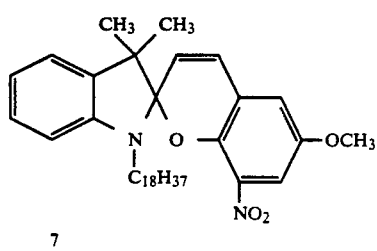

The thus obtained spiropyran is brominated according to the procedure shown in the following step.

STEP 5

1.1 g (6.0 mmols) of N-bromosuccinimide is dissolved in 500 ml of a mixed solvent of acetic acid and chloroform at a mixing ratio by volume of 1:1. An acetic acid solution of 1.6 g (2.7 mmols) of spiropyran of the formula (7) is dropped in the mixture in 30 minutes. After one hour, the reaction solution is poured into a mixture of chloroform and sodium hydroxide, followed by extraction with chloroform. The organic phase is dried and concentrated, followed by purification with column chromatography and recrystallization twice from ethanol to obtain 30 ml of spiropyran (SP-B). The reaction sequence is shown below.

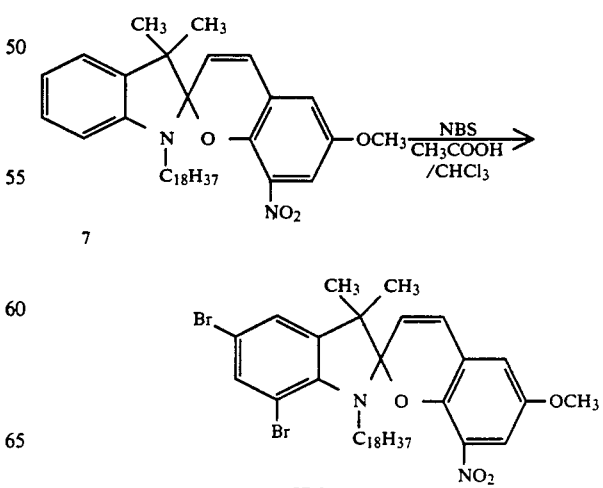

The chemical structure of the final product is confirmed by NMR. The attributions of the respective spectra of NMR are shown in Table 1 below.

TABLE 1

Attributions of NMR of SP-B

| Chemical Shift | Attribution | Number of H Atoms |
| --- | --- | --- |
| 0.88(t) | methyl at an end of a long chain J = 6.4 Hz | 3 |
| 1.10(s) | 3'-methyl | 3 |
| 1.25(m) | long-chain methylene | 32 |
| 1.30(s) | 3'-methyl | 3 |
| 1.62(t) | methylene at the β position of the indoline, J = 4.8 Hz | 2 |
| 3.47(t) | methylene at the α position of the indoline, J = 4.8 Hz | 1 |
| 3.48(t) | methylene at the α position of the indoline, J = 10.3 Hz | 1 |
| 3.80(s) | methoxy | 3 |
| 5.80(d) | 3-olefin J = 10.0 Hz | 1 |
| 6.85(d) | 3-olefin, Hz J = 10.0 Hz | 1 |
| 6.87(d) | 4'-hydrogen J = 3.2 Hz | 1 |
| 7.01(d) | 5-hydrogen, J = 2.0 Hz | 1 |
| 7.24(d) | 6'-hydrogen, J = 3.2 Hz | 1 |
| 7.38(d) | 7-hydrogen, J = 2.03.2 Hz | 1 |

Note: The unit in the chemical shift is ppm and the letters in the parentheses indicate the shape of a peak, i.e. s: singlet, d: doublet, t: triplet and m: multiplet, and the "J" in the attribution indicates a coupling constant.

When a DMF solution of SP-B is irradiated with a UV ray (366 nm), the colorless solution is quickly turned into a colored solution, with an absorption maximum of 673 nm. This solution is sensitive to light with a wavelength of 700 nm. When a visible light ray of 700 nm is irradiated, the colored solution is quickly turned into a colorless solution. These changes are reversible. These changes are repeated 100 times or more, whereupon no changes in the absorption spectrum of the colorless and colored products is observed. The absorption spectra of the colorless and colored products are shown in the sole figure wherein the spectrum chart A is for the colorless product and the spectrum chart B is for the colored product.

The SP-B compound shows good photochromic characteristics in other solvents. The absorption maximum wavelengths of the colored product in various solvents are summarized in Table 2.

TABLE 2

| Solvent | Absorption Maximum |
| --- | --- |
| ethanol | 645 nm |
| dimethylformamide | 673 nm |
| tetrahydrofuran | 645 nm |
| benzene | 649 nm |

When iodo compounds having from 1 to 30 carbon atoms are used instead of iodooctadecane, the preparation and photochromic characteristics are similar to those of the above procedure. For instance, the above procedure is repeated using, instead of idodooctadecane, iodomethane, iodooctane and iodotriacontane, thereby obtaining spiropyran compounds having at the N position a methyl group, an octyl group and a triacontyl group. It will be noted that although spiropyran compounds having a larger number of carbon atoms cannot be prepared because starting iodo compounds are not available, similar characteristics are considered to result. The absorption maximum wavelengths of the colored products, in dimethylformamide, of the spiropyran compounds obtained above are shown in Table 3.

TABLE 3

| Substituent At N Position | Absorption Maximum (nm) |
| --- | --- |
| methyl | 670 |
| octyl | 672 |
| triacontyl | 671 |

What is claimed is:

1. A photochromic spiropyran compound of the following formula

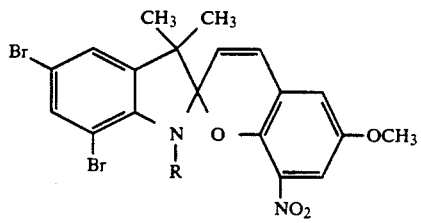

wherein R represents an alkyl group having from 1 to 30 carbon atoms.

2. A photochromic spiropyran compound according to claim 1, wherein the alkyl group has from 16 to 20 carbon atoms.

* * * * *